(12) United States Patent
House

(10) Patent No.: US 11,534,577 B2
(45) Date of Patent: Dec. 27, 2022

(54) CATHETERS HAVING LOW VISCOSITY LUBRICANT

(71) Applicant: Adapta Medical, Inc., Colorado Springs, CO (US)

(72) Inventor: Jamie Glen House, Colorado Springs, CO (US)

(73) Assignee: ADAPTA MEDICAL, INC., Colorado Springs, CO (US)

( * ) Notice: Subject to any disclaimer, the term of this patent is extended or adjusted under 35 U.S.C. 154(b) by 74 days.

(21) Appl. No.: 16/457,835

(22) Filed: Jun. 28, 2019

(65) Prior Publication Data

US 2020/0001049 A1 Jan. 2, 2020

Related U.S. Application Data

(60) Provisional application No. 62/691,360, filed on Jun. 28, 2018.

(51) Int. Cl.
| | | |
|---|---|---|
| *A61M 25/01* | (2006.01) | |
| *A61M 25/00* | (2006.01) | |
| *A61L 29/14* | (2006.01) | |
| *A61M 25/06* | (2006.01) | |

(52) U.S. Cl.
CPC ....... *A61M 25/0111* (2013.01); *A61M 25/002* (2013.01); *A61L 29/14* (2013.01); *A61M 25/0017* (2013.01); *A61M 2025/0059* (2013.01); *A61M 2025/0062* (2013.01); *A61M 2025/0681* (2013.01); *A61M 2210/1092* (2013.01)

(58) Field of Classification Search
CPC ............ A61M 25/0111; A61M 25/002; A61M 2210/1092; A61M 25/0017; A61M 2025/0062; A61M 2210/1096; A61M 2025/0046; A61M 25/0113; A61L 2400/10
See application file for complete search history.

(56) References Cited

U.S. PATENT DOCUMENTS

| | | | |
|---|---|---|---|
| 3,967,728 A * | 7/1976 | Gordon | A61M 25/002 206/484 |
| 9,308,298 B2 * | 4/2016 | Zhang | A61M 25/0045 |
| 2004/0074794 A1 * | 4/2004 | Conway | A61M 25/002 206/364 |

(Continued)

OTHER PUBLICATIONS

Ozbek, H., Viscosity of Aqueous Sodium Chloride Solutions from 0-150C, 1977, Lawrence Berkeley National Laboratory. (Year: 1977).*

(Continued)

*Primary Examiner* — Tatyana Zalukaeva
*Assistant Examiner* — Hans Kaliher
(74) *Attorney, Agent, or Firm* — Moazzam & Associates, LLC

(57) ABSTRACT

A closed-system urinary catheter with a low viscosity gel lubrication is disclosed. The system has an uncoated catheter, but a hydrophilic coated catheter could be used. The low viscosity lubricating gel within the sachet uniformly coats the catheter when the sachet is ruptured just prior to use. A low viscosity lubrication gel could alternatively be place in the area inside the sheath and external to the catheter. Therefore, the variability that occurs with a hydrophilic catheter or the areas of a non-lubricated catheter with the higher viscosity gel catheters is avoided.

20 Claims, 3 Drawing Sheets

(56) References Cited

U.S. PATENT DOCUMENTS

| | | | |
|---|---|---|---|
| 2009/0099531 A1* | 4/2009 | Griesbach, III | A61M 25/002 206/571 |
| 2010/0312203 A1* | 12/2010 | House | A61F 5/4405 216/33 |
| 2011/0230864 A1* | 9/2011 | House | A61M 25/0111 604/544 |
| 2015/0011981 A1* | 1/2015 | House | A61M 25/0009 264/249 |
| 2017/0340857 A1* | 11/2017 | Ryan | A61M 25/002 |
| 2019/0240445 A1* | 8/2019 | Palmer | A61M 25/002 |

OTHER PUBLICATIONS

Ozbek, H., Viscosity of Aqueous Sodium Chloride Solutions from 0-150C, 1977, Lawrence Berkeley National Laboratory. (Year: 1977) (Year: 1977).*

* cited by examiner

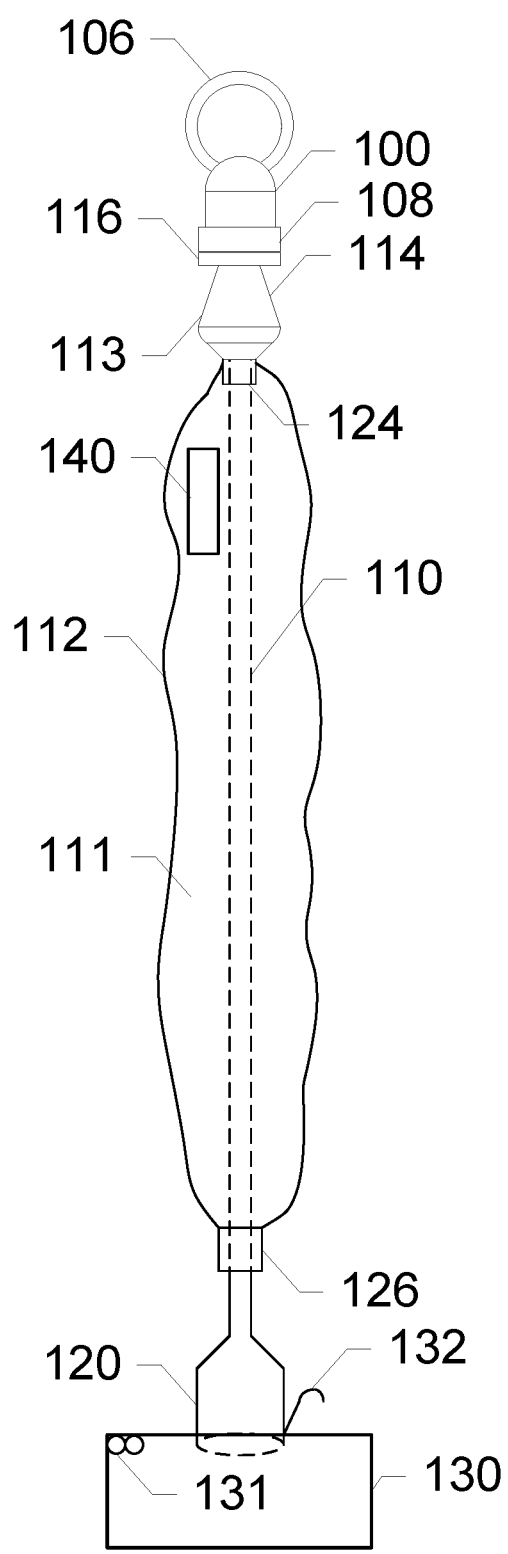
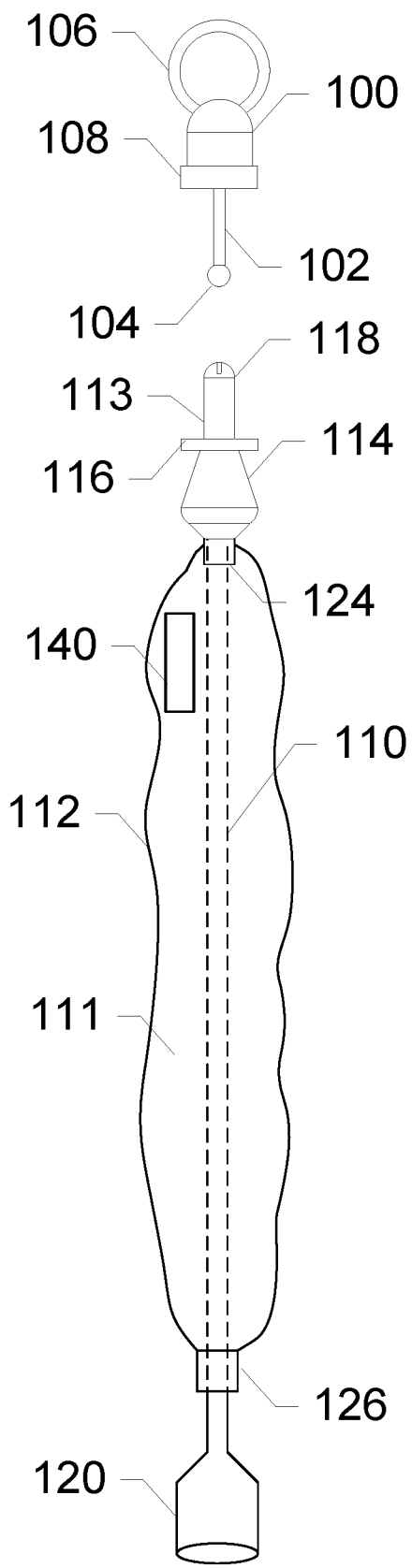
FIG. 2A  FIG. 2B

CATHETERS HAVING LOW VISCOSITY LUBRICANT

This U.S. Patent Application claims priority to U.S. Provisional Patent Application Ser. No. 62/691,360, filed Jun. 28, 2018, the content of which is hereby incorporated by reference herein in its entirety into this disclosure.

BACKGROUND OF THE SUBJECT DISCLOSURE

Field of the Subject Disclosure

The present subject disclosure relates to urinary catheters. More specifically, the present subject disclosure relates to urinary catheters having low viscosity lubricants.

Background of the Subject Disclosure

Intermittent catheterization of an individual's urinary bladder is a common practice today for many persons who are in a hospital setting, a nursing home, doctor's office, rehabilitation facility, or at home. For instance, a patient is sometimes catheterized to treat such conditions as urinary retention, the inability to evacuate urine, or for the purpose of obtaining a sterile urine specimen from a patient in a doctor's office or at home.

The need for intermittent catheterization of an individual sometimes arises due to problems typically associated with long term use of indwelling catheters, such as infections, urethral damage, and bladder damage. Long term use of an indwelling catheter is also a risk factor for bladder cancer. This is often the case for persons having a neurogenic urinary condition (neurogenic bladder), such as in a spinal cord injury, multiple sclerosis, stroke, or brain injury. Conditions that interfere with the individual's ability to voluntarily void the bladder may also arise post-surgically or as a result of benign prostatic hypertrophy, prostate cancer or diabetes mellitus. Many of the affected individuals are capable of, and would prefer to perform, self-catheterization.

For many, the level of risk and discomfort of repeated catheterizations carried out over the course of a day (at 3-6 hour intervals, for example) are offset by the accompanying convenience, privacy or self-reliance that is achieved. Some of the major difficulties that arise in self-catheterization are the lack of satisfactory catheterization kits, the problem of maintaining the required level of sanitation during the procedure, and the difficulty of sometimes performing the procedure under conditions of restricted space and privacy.

In most closed-system sterile units the collection bag doubles as a sterile cover. These catheters are extremely difficult for the user to grasp and insert. Many of these closed-system catheters have a cap that covers the introducer tip to maintain sterility. This is particularly a problem for self-catheterization users who may also have neurological problems that limit manual dexterity, because they have difficulty removing the cap. Also, with some of the available catheter kits and methods, the catheter is either not sufficiently lubricated during insertion (and thus requires the additional application of possibly non-sterile lubricant), or the catheter is too slick with lubricant and cannot effectively be grasped through an insufficiently flexible bag. As a practical matter, many individuals who would prefer to self-catheterize cannot conveniently do so using many of the existing catheterization apparatus while still maintaining the required level of sanitation.

Many catheterization tasks require a degree of dexterity to accomplish. People with normal dexterity, like paraplegics, may not have use of their lower extremities, but their hands have normal function. Some quadriplegics can have use of their upper extremities, having absolutely normal movement, like a paraplegic, except they lack normal hand dexterity. Thus, many tasks requiring a degree of hand dexterity are very difficult for quadriplegics to accomplish.

Spinal cord injuries at the fifth, sixth, and seventh cervical vertebrae level (C5, C6, C7) affect the use of a person's hands and make these tasks difficult or impossible with current products. Moreover, people who have had strokes, brain injuries, or multiple sclerosis may also require catheterization but have limited dexterity. The current catheterization market does not currently support the needs of these individuals.

Insertion of a lubricated catheter is one such task. Devices currently on the market allow for different ways of lubricating a catheter. However, most of these closed-system catheter units have gel covering the catheter within the bag, which makes it difficult or impossible to grasp with limited dexterity and insert into the bladder. Another problem with the current closed-system catheters is that the catheter may not be circumferentially lubricated or the gel may be wiped away as it is pushed through the non-lubricated introducer tip. This can lead to urethral irritation, "sticking", and discomfort or pain for the recipient. Some closed-system hydrophilic catheter are bathing in fluid and are therefore difficult to manipulate.

SUMMARY OF THE SUBJECT DISCLOSURE

The present subject disclosure describes catheter devices, systems, and methods that contain a low viscosity lubricant in a sachet contained within the sheath that surrounds the catheter. The sachet may have an area that is weakened in manufacturing (or the entire sachet may be breakable) such that it is able to allow the low viscosity gel to pour out onto the catheter within the sheath when the sachet is compressed by someone with limited dexterity.

The present subject disclosure addresses long felt needs in the field of catheters, in particular, urinary catheters. Urinary catheters require lubrication prior to insertion into the urethra. The two options today include placing a small amount of higher viscosity water-soluble gel [Cp (centipoise) usually ranging from 15,000-30,000] on the catheter or using a hydrophilic coating of the catheter combined with a water or saline wetting fluid. The higher viscosity gel catheters are more difficult to insert for individuals with limited hand dexterity because of friction resistance. The hydrophilic catheters are very slick and easier to insert than high viscosity gel covered catheters, but can still be very difficult to manipulate and insert because of this slickness. The hydrophilic catheters and their coating may also be affected by environmental controls.

The present subject disclosure uses a low viscosity water-based gel which quickly travels down and covers the catheter after the sachet is ruptured just prior to use. This gives a functionality to the catheter insertion similar to a hydrophilic catheter, but without the difficulty in grasping the catheter with the sheath. The low viscosity lubricating gel ensures that there are no uncoated dry spots on the catheter during insertion, which often happens with the higher viscosity standard gel (Cp 15,000-30,000). No other catheters on the market use an uncoated catheter with a low viscosity water-based gel, preferably contained within a sachet.

The present subject disclosure describes an uncoated catheter, but could also be combined with a hydrophilic coated catheter. The low viscosity lubricating gel within the sachet uniformly coats the catheter when the sachet is ruptured just prior to use. Therefore, this prevents the variability that occurs with either a hydrophilic catheter or a non-lubricated catheter with high viscosity gel.

In one exemplary embodiment, a urinary catheter according to the present subject disclosure has a proximal end that enters the patient first. The distal end of the catheter is inserted into a port that is attached to the urine collection bag. The proximal end of the catheter sits in the guide mechanism which is the distal end of the introducer. The cap and stem mechanism covers a 1 cm part of the introducer that enters the urethra. The area between this insertable part and the expanded gripping device is a radial phalange that acts as a stop mechanism when inserting the introducer into the urethra. A pliable and cylindrical sheath is attached via heat shrink to the guide portion of the introducer. It also attaches to the port component on the proximal end of the urine collection bag. A low viscosity liquid gel is in a sachet that is located within the sheath and external to the catheter. When this is sachet is ruptured, typically right before use of the catheter, liquid gel flows upon the urinary catheter that is located within the sheath. No liquid gel touches the user's hands because it is enclosed within the sheath.

In one exemplary embodiment, the present subject disclosure is a catheter system. The system includes a catheter; a sheath surrounding the catheter; and a sachet positioned within the sheath and external to the catheter, the sachet containing a lubricating fluid having a viscosity of less than 2,000 cP.

In another exemplary embodiment, the present subject disclosure is a catheter system. The system includes a catheter; a sheath surrounding the catheter; a collection bag positioned at one of the catheter; and a sachet comprised of a pliable foil and plastic and positioned within the sheath and external to the catheter, the sachet containing a lubricating fluid having a viscosity of less than 2,000 cP.

In yet another exemplary embodiment, the present subject disclosure is a catheter system. The method includes a catheter; a sheath surrounding the catheter; a collection bag positioned at one of the catheter; an introducer coupled to a proximal end of the catheter, the introducer in liquid communication with a volume between the sheath and the catheter; and a sachet comprised of a pliable foil and plastic and positioned within the sheath and external to the catheter, the sachet containing a lubricating fluid having a viscosity of less than 2,000 cP.

BRIEF DESCRIPTION OF THE DRAWINGS

FIG. 2A shows a catheter assembly with a collection bag, according to an exemplary embodiment of the present subject disclosure.

FIG. 2B shows a catheter assembly with the cap removed, according to an exemplary embodiment of the present subject disclosure.

DETAILED DESCRIPTION OF THE SUBJECT DISCLOSURE

Figure 1A:
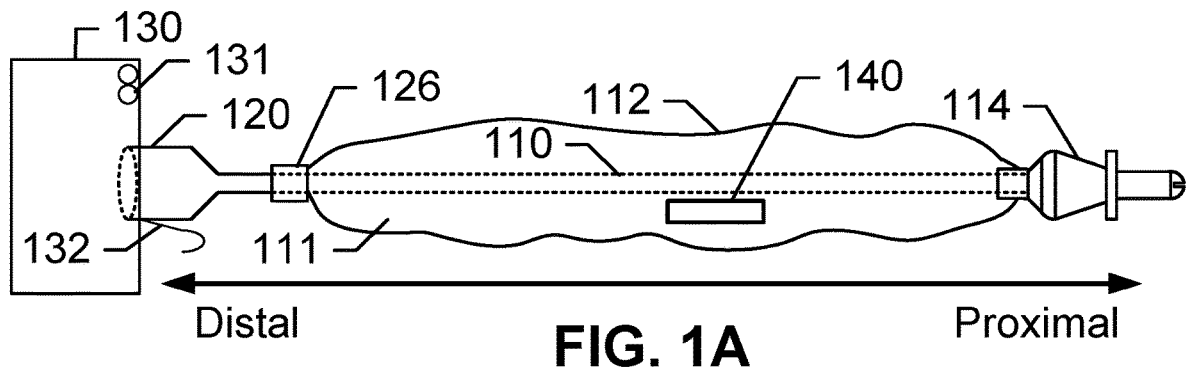
FIG. 1A shows a catheter assembly, according to an exemplary embodiment of the present subject disclosure.
Figure 1B:
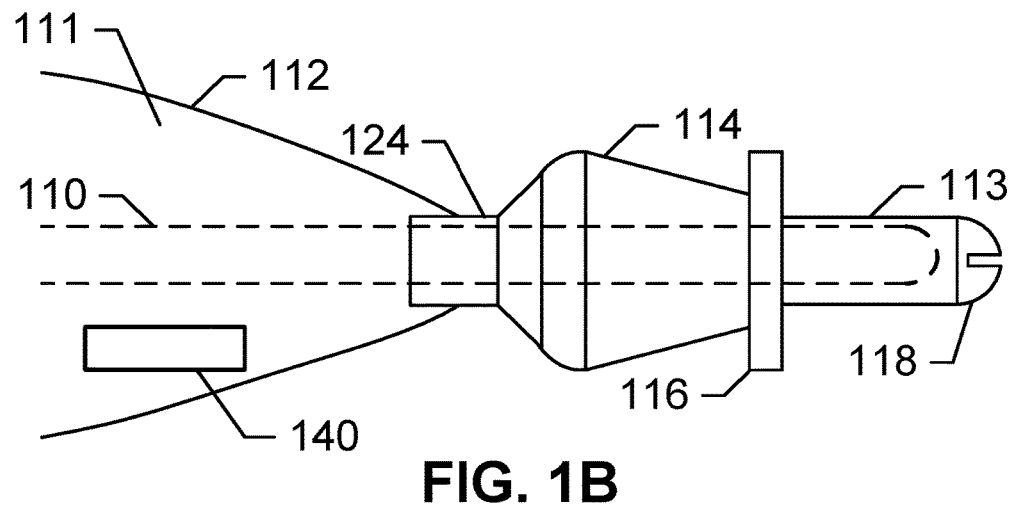
FIG. 1B shows more detail of the introducer portion of a catheter assembly, according to an exemplary embodiment of the present subject disclosure.

The present subject disclosure addresses the shortcomings of conventional catheters, as discussed above. In various exemplary embodiments, the present subject disclosure describes disposable lubricating catheterization assemblies used for inserting a catheter into the urethra of an individual for the purpose of evacuating the bladder. The catheter assembly includes a substantially rigid catheter introducer with a member for positioning the introducer tip against the urethral opening or into the first part of the urethra, a flexible catheter and a flexible thin-walled sheath surrounding the catheter and optionally partially covering the catheter introducer. The catheter introducer may include an insertion tip portion, a gripping portion, and a catheter guide portion. The lubricant is a low viscosity gel in a contained housing, such as a sachet, which is ruptured prior to use and coats the catheter within the sheath, in order to facilitate grasping of the catheter and feeding of the tube into the urethra and into the bladder.

A catheterization assembly in accordance with the present subject disclosure is suitable for use for self-catheterization in the home, a public restroom, a busy emergency room or clinic office, and elsewhere, and lessens the chances of contamination and subsequent infection of the urinary tract. The catheterization assembly is also ideal for medical settings where it is important but difficult to maintain sterile technique, such as an emergency room or medical clinic. The improved easy-to-use disposable catheterization kit is also economically practical for use for temporary catheterizations in hospitals, mobile emergency facilities, doctors' offices, rehabilitation facilities, nursing homes and the like. This design is specially made to allow individuals with limited dexterity the ability to perform intermittent self-catheterization.

As stated above, urinary catheters require lubrication prior to insertion into the urethra. The two options today include a small amount of higher viscosity gel on the catheter or a hydrophilic coating of the catheter and a wetting fluid. The higher viscosity gel catheters are typically more difficult to insert for individuals with limited hand dexterity. The hydrophilic catheters are usually very slick, so can be very difficult to manipulate and insert because of the slickness. The hydrophilic catheters are also at times affected by the environmental controls. The present subject disclosure claimed here addresses these shortcomings of conventional devices and techniques.

According to the present subject disclosure, a closed-system urinary catheter may have an uncoated catheter surrounded by a pliable protective sheath. Within the sheath is a low viscosity lubricating water-based gel. More specifically, a contained housing, such as a sachet, is used to contain the lubricating gel prior to use and catheter insertion. By rupturing the sachet, the low viscosity lubricating gel covers the uncoated catheter completely and provides a lubrication to the catheter tube that provides characteristics which fall between the commonly used, high viscosity, thick lubricating gel covered catheter, and the also commonly used hydrophilic catheter. This allows for easy insertion into the urethra for individuals with limited dexterity but is not easily affected by the environment ensuring the patient receives a catheter that is ready to use when needed and its gel has maintained its integrity.

The present subject disclosure differs in a number of ways from what currently exists in the marketplace. The present product may include an uncoated catheter that sits within a protective sheath. This protective sheath is made of a material that improves the ability to grasp the catheter. A sachet that holds between 3 and 15 mL of low viscosity (<2,000 cP) water-based lubricating gel prevents the gel from contacting the catheter until just seconds or minutes prior to use. In an exemplary embodiment, the viscosity of the lubricating fluid is 300-600 cP. This sachet maintains the low viscosity lubricating gel in the best possible condition by preserving it and thereby maintaining its intended qualities. Gels that are exposed to air have a greater propensity to age and lose their viscosity and thereby decrease their lubricating characteristics. Specifically, the present catheter system functions best if the viscosity is 2,000 cP or less. As used herein and throughout this disclosure, "low viscosity" in describing the lubricating gel is defined as 2,000 cP or less.

Hydrophilic catheters are commonly used in the field, but are limited by their higher price and the possibility of being affected by environmental factors such as humidity, heat, and freezing temperatures. Other adverse possibilities related to environmental concerns are mechanical bending of the catheter, which could include cracking or flaking which can create an uneven surface and friction against the urethra during insertion. This could be a factor that affects the sensation or mechanical changes of the patient's urethra. Other factors with the hydrophilic catheters are the possibility of sticking to the urethra during insertion or removal and the possibility of burning the urethra. The chemical makeup of the hydrophilic coating is a variable that is different between different manufacturer's hydrophilic catheter products. Hydrophilic catheter coating material often flakes off into the wetting-fluid and may enter the bladder lumen and create a nidus for stone formation or urinary tract infection.

High viscosity gel catheters are typically more difficult to insert and may not be evenly and uniformly coated. Studies have shown that high viscosity gel catheters may cause irritation and even scarring of the urethra. Scarring is in the form of strictures which may create a situation that prevents catheter insertion in the future and/or require surgical intervention.

The present subject disclosure addresses the shortcomings of the various conventional urinary catheters by providing a separately packaged gel insert which maintains the integrity of the gel and prevents it from breaking down before its use. In an exemplary embodiment, the present catheter includes an uncoated catheter with a sheath containing a sachet therein. A low viscosity lubricating gel within the sachet uniformly coats the catheter when the sachet is ruptured just prior to use. Therefore, this low viscosity gel covers the catheter only when needed and eliminates the variability that occurs with a hydrophilic catheter and a non-lubricated catheter with high viscosity gel.

Throughout the disclosure, components of the subject disclosure may include a proximal end and a distal end. The proximal end describes an end of the component nearest the point of insertion into the urethra of a user. The distal end describes an end of the component farthest away from this point of insertion. When proximal and distal are used as adjectives to distinguish elements, the proximal element is closer to the proximal end and the distal element is closer to the distal end.

For the following description, it can be assumed that most correspondingly labeled structures across the figures having the same last two digits (e.g., 110, 210, 310, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIGS. 1A, 1B, 2A, and 2B show a system for housing and delivering a volume of low viscosity lubricating gel prior to use, according to an exemplary embodiment of the present subject disclosure. In this embodiment, the system includes a catheter 110, a sheath 112 surrounding catheter 110, a catheter introducer tip 113, an introducer 114 coupled to the catheter introducer tip 113, an outlet 120, and a catheter cap 100. Catheter 110, sheath 112, catheter introducer tip 113, introducer 114, and outlet 120 are generally described, for instance, in commonly owned U.S. Pat. No. 6,090,075, issued on Jul. 18, 2000, the contents of which are incorporated hereby incorporated by reference herein in their entirety.

Catheter 110 is generally a flexible tube for evacuating urine from the bladder of the user. Catheter 110 is inserted into the urethra of the user using catheter introducer tip 113. Catheter 110 has a proximal end and a distal end. At or near the proximal end is a urine inlet. At the distal end of catheter 110 is outlet 120. The catheter 110 may be comprised of PVC, silicon, rubber or other suitable material type, as known to one having ordinary skill in the art. Alternatively, a hydrophilic catheter could be used, but is not a requirement because of the use of a sachet 140 containing gel, as described herein.

The sheath 112 may be comprised of a material that is pliable and aids in grasping the catheter. It may be cylindrical or semi-cylindrical and attaches to the designated part of the introducer tip 113. Alternatively, the sheath 112 may attach to various closure points or areas, such as 126.

Sheath 112 surrounds catheter 110 and provides protection for catheter 110. Sheath 112 has a proximal end, a distal end, a lumen 111, and closure point 126. The proximal end of sheath 112 connects to the distal end of catheter introducer tip 113 at a proximal closure point. The distal end of sheath 112 connects to the distal end of catheter 110 or outlet 120 at a distal closure point 126. These closure points such as 126 may use any type of tie, band, adhesive, sealing mechanism, etc., in order to attach sheath 110 at these points. Lumen 111 is generally the space between catheter 110 and the material of sheath 112 surrounding catheter 110. Lumen 111 is large enough to house a sachet 140 and permit catheter 110 to rotate and slide therein when sheath 112 collapses and is gathered up during use, yet is not so large that sheath 112 is cumbersome. Sheath 112 generally benefits from a means of venting to allow air to escape as sheath 112 is bunched together during insertion. This may be accomplished through vents in sheath 112 located anywhere on sheath 112. However, because introducer 114 does not require a membrane, venting may occur through catheter introducer tip 113 when catheter cap 100 is removed.

Catheter introducer tip 113 is generally a guide for inserting catheter 110 into the urethra of the user. Introducer 114 includes a catheter introducer tip 113 having a proximal tip end 118, an insertion stop point 116, and a guide portion 124. Catheter introducer tip 113 has a longitudinal through-bore with a bore diameter that is at least as large as catheter 110's outer diameter, so that catheter 110 can rotate and slide through the throughbore. The elongated tip 113 is generally sized such that it fits into the opening of the urethra of the user. At the base of introducer tip 113 is an insertion stop point 116. Insertion stop point 116 is a radial flange generally between elongated tip 113 and introducer 114. Insertion stop point 116 prevents further insertion of catheter introducer tip 113 into the urethra. Insertion stop point 116 also serves as a coupling point with catheter cap 100, such that a lip 108 of catheter cap 100 may surround insertion stop point 116 when coupled. The proximal edge of insertion stop point 116 may be a beveled edge, such that catheter cap 100 may easily fit over insertion stop point 116 and secure to the distal edge of insertion stop point 116. Alternatively, it could be solid for gripping.

The introducer 13 includes an elongated tip 18 comprised of silicon or similar material that extends beyond the radial phalange or insertion stop 16 by approximately 1 cm-1.5 cm. This elongated tip 18 enters the urethra and bypasses a significant amount of bacteria. The flange 116 may be circular, square, or any other variable shape that prevents the introducer 114 from entering the urethra beyond the 1 cm-1.5 cm extension. The elongated tip 113 that enters the urethra is crosscut at its proximal tip so that the catheter 110 can exit the introducer easily and enter the urethra. The introducer portion that is opposite the elongated tip 113 may include a surface area that allows for the sheath 112 to be attached. See, for example, FIG. 3. Methods of attachment of the sheath 112 to the introducer tip 113 can include, but are not limited to, shrink, collar, ultrasonic welding, etc.

The sachet 140 is filled with a low viscosity water-based gel. Viscosity is in the range of 100-2000. It is made of a material that prevents evaporation and is stable in transport, but with the appropriate amount of force can be ruptured or fractures, expelling the low viscosity gel. The volume of gel that is contained within the sachet 140 ranges from 3 mL-15 mL. The liquid may be sterilized via gamma or e-beam radiation. After the sachet 140 is ruptured and the gel is expelled, the material that the sachet is made of is pliable and does not interfere with the scrunching of the sheath 112 as the distal end moves closer to the proximal end and the catheter 110 enters the bladder. If this sachet 140 were more rigid, it would likely resist collapsing of the sheath 112 and interfere with insertion of the catheter 110 into the bladder. The sachet 140 may be made of, for example, a thin and pliable plastic such as foil.

When catheter 110 is being inserted, catheter 110 travels through introducer 114. Introducer 114 has a proximal end and a distal end. The proximal end of introducer 114 has an opening in its tip end 118 at elongated introducer tip 113, while the distal end has a distal opening extending to the guide portion 124. The guide portion 124 is at the distal end of catheter introducer tip 113, and is near where sheath 112 secures to catheter introducer tip 113 at proximal closure point. Before insertion into the urethra, the proximal end of catheter 110 is positioned in the guide portion 124, ready to be pushed through catheter introducer tip 113.

Outlet 120 is at the distal end of catheter 110. Outlet 120 allows catheter 110 to attach, for instance, to a urine collection bag 130, a drain, etc. The urine collection bag 130 may be comprised of plastic and is attached to the distal end of the catheter 120 or sheath 112. The bag 130 may include one or more thumb holes 131 (not shown actual size) at top of the bag 130 that allow for easy tear-away opening to assist urine drainage from the bag for individuals with limited dexterity. Further, a hook 132 (not shown actual size) may be attached to the distal end 120 of the catheter 110 and the proximal end of the urine collection bag 130 where the two meet. This allows the user the ability to hang the bag 130 on a chair or another object while the urine collection bag 130 is filling with urine. This allows the user to use both hands for the purpose of catheterization instead of attempting to hold the urine collection bag 130 with one hand as it becomes heavy when it fills with urine.

As shown in FIGS. 2A-2B, catheter cap 100 may be removably coupled to catheter introducer tip 113. When coupled to catheter introducer tip 113, catheter cap 100 snaps around or otherwise secures to insertion stop point 116, covering the elongated tip 113. Catheter cap 100 prevents airflow into the elongated tip 113. An elongate stem 102 of catheter cap 100 extends into the elongated tip 113 and through introducer 114 to seal the distal opening of introducer 114. Elongate stem 102 includes a stopper 104 at the distal end of elongate stem 102. Stopper 104 is sized such that it releasably engages with the distal opening at the base of introducer 114 in order to seal the distal opening. For example, stopper 104 may be a spherical shape which fits into a semi-spherical distal opening at the base of introducer 114. Stopper 104 may also simply be the distal end of elongate stem 102. The size and shape of stopper 104 and the distal opening may be designed based upon the desired amount of force necessary to remove catheter cap 100. Catheter cap 100 may further include a ring 106. Ring 106 is preferably sized to fit a finger or thumb easily. Ring 106 may be used to remove catheter cap 100 from introducer tip 113. Ring 106 allows users having limited manual dexterity to more easily remove catheter cap 100 from introducer tip 113, allowing a greater amount of force to hold the seal.

As shown more clearly in FIG. 2B, a cap 100 has a ring 106 at the top and a stem 102 that runs from the inside of the cap 100 and extends approximately 1 inch. This is made so that it inserts through the introducer elongated tip 113 and to plug the guide 124. The guide 124 is the area that the sheath 112 is attached to. The stem 102 then is pulled out of the elongated tip 113 prior to use and helps to pre-lubricate the pathway in the tip 113 that the catheter 110 will travel. This helps to ensure the catheter 110 remains lubricated prior to insertion.

The low viscosity gel which is released by compromising the sachet 140 also ensures that the catheter 110 is fully and evenly lubricated during this process. The cap 100 also contains approximately 1 milliliter of higher viscosity gel that is similar to other products. This pre-lubricates the first portion of the tip 118 prior to insertion. After the stem 102 is pulled out of the introducer tip 113, it can then be used to evenly spread this higher viscosity gel evenly over the external portion of the introducer tip 113. This ensures the introducer tip 113 entering the first part of the urethra is thoroughly lubricated. Conventional catheter systems in the market with introducer tips do not have this mechanism and often have dry or partially lubricated introducer tips entering the urethra.

In use, the catheter system according to the present subject disclosure may be packaged as a kit, and ready to use by an end user, who may be a medical professional or a patient. A user opens the package and pulls out the closed-system catheter. Just prior to use, the user would compress or rupture the sachet 140 that is located within the sheath 112 and external to the catheter 110. This causes the low viscosity liquid gel to flow on the catheter 110 and coating the part of the catheter 110 that will enter the urethra. The user then removes the cap 100 and stem 102 component by pulling it out of the introducer tip 113. There will be a small amount of high viscosity gel in the cap 100 that is partially coating the 1 cm portion 113 of the introducer 114 that will enter the urethra. The user then takes the lubricating stem 102 and spreads the high viscosity (18,000-26,5000 Cp) gel (standard, thicker type) evenly over the introducer tip 113 that will enter the urethra. The user then inserts the proximal 1 cm portion 113 of the introducer tip 113 into the urethra up until the radial flange stop 116. Once it is in the urethra the radial phalange 116 prevents it from entering too far. The user then grabs the sheath 112 and catheter 110 and inserts the catheter 110 into the bladder. The sheath 112 then collapses on itself allowing the catheter 110 to enter the bladder. Urine then flows in the urine collection bag 130. When urine stops flowing, the catheter 110 is removed and the entire product is discarded into an appropriate receptacle.

From a practical use perspective, an individual would take the catheter system out of the packaging. The user would then rupture the sachet 140 by applying pressure between the palms of their hands, within their fingers, or on a hard surface by compressing it. This would cause the low viscosity liquid gel to flow from the sachet 140 within sheath 112 and onto the catheter 110. The user would then rock the catheter 110 back-and-forth so that the liquid gel covers the urinary catheter 110 that will be inserted into the urethra or at least the first proximal half. The user would then take off the cap 100 and lubricating stem 102. The user would then use the end 104 of the lubricating stem 102 to spread the high viscosity gel that is in the introducer tip 18 so that it is evenly covered with gel. The user would then insert the introducer tip 113 into the first 1 cm of the urethra. Once it is in the urethra the catheter 110 would then be inserted into the bladder. Once the bladder has completely drained by the catheter 110, it is pulled back into the sheath 112. The urine collection bag 130 (not shown actual size) can be drained into the toilet after tearing it open with the two loophole tearing mechanism 131 (not shown actual size). This can be done by using the loops 131 on the urine collection bag that are pulled apart at a pre-designed tear area. After the urine is drained into the toilet, the entire catheter system is thrown into the trash or an appropriate disposable location.

There are many ways to create the device or system described in the present subject disclosure. One such exemplary technique may be used. It should be appreciated that many other ways of making the package are possible and within the scope of the present subject disclosure, as recognized by one having ordinary skill in the art after considering the present disclosure. The individual parts of the present device/system are combined together to make a "kit." The catheter tube 110 proximal end is inserted into the guide mechanism 124 of the introducer 114. The distal end of the catheter is inserted into a port tube 120 attached to a urine collection bag 130. A sheath 112 is placed over the catheter 110 and using heat shrink (or another mechanism to adhere the sheath can be used such as a clamp) applied to the sides over the end part of the sheath on both sides 126. This attaches the sheath 112 to the guide mechanism 124 of the introducer tip 113 and the distal end 120 of the catheter 110 or port tube. The cap 100 and lubricating stem is filled with gel in the cap portion and then inserted through the introducer tip 113 to where they snuggly fits against the introducer tip 113 and the distal stem 102 is in the junction between the gripping mechanism and the guide 124. A sachet 140 filled with liquid gel with a low viscosity (200-2,0000 Cp) is placed within the sheath 112 prior to sealing the heat shrink or clamp around the proximal and distal ends of the sheath. The entire system is placed within a package and then sterilized. In some embodiments, it may be possible to fill the sheath 112 with liquid gel and prevent the need for the sachet 140, or fill the sheath 112 with gel in addition to the gel that is in the sachet 140.

Figure 3:
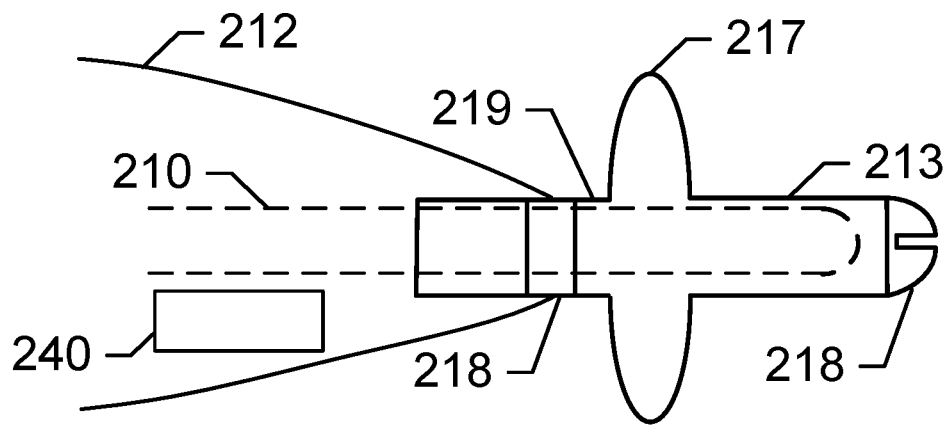
FIG. 3 shows an introducer portion of a catheter assembly, according to another exemplary embodiment of the present subject disclosure.

FIG. 3 shows another exemplary embodiment of the introducer portion of the catheter assembly. In this embodiment, a catheter 210 is slideable within the body of an introducer 213 having a radial flange 217. The introducer 213 has an elongated proximal tip portion 218 through which the catheter 210 slides into a urethra. The flange 217 acts as a stop to prevent the elongated tip portion 218 of the introducer from penetrating the urethra more than a given length, which is about 1 cm or less. A sachet 240 is contained within the sheath 212 and external to the catheter 210. In this exemplary embodiment, the sheath 212 is directly adhered to a distal portion 219 of the introducer, positioned on an opposite end to the elongated introducer tip 218, through a collar 218, heat shrink or other mechanism appreciated by one having ordinary skill in the art. The use, function, and mechanism of operation of this embodiment is substantially the same as that described for the embodiment shown above in FIGS. 1-2, so it will not be repeated here again for sake of clarity.

Figure 4:
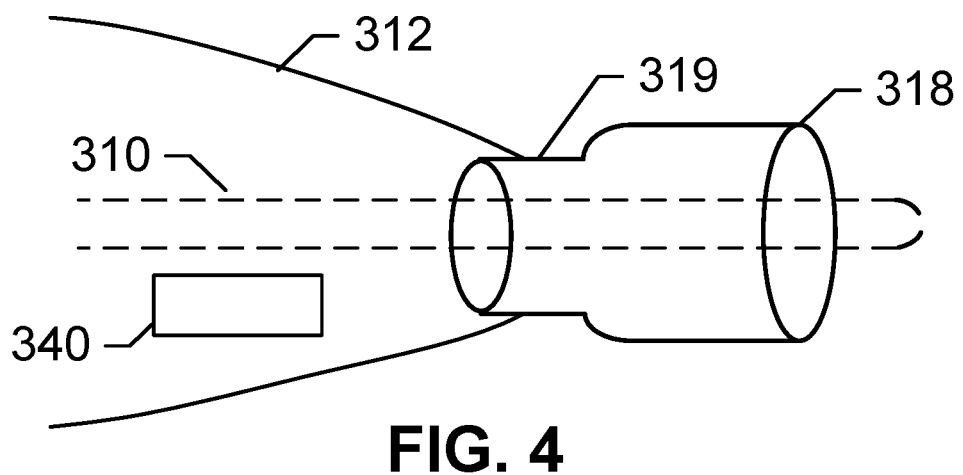
FIG. 4 shows an introducer portion of a catheter assembly, according to another exemplary embodiment of the present subject disclosure.

FIG. 4 shows another exemplary embodiment of the introducer portion of the catheter assembly. In this embodiment, a catheter 310 is slideable within the body of a cup-shaped, cylindrical introducer 318 having a smaller cylindrical portion 319 positioned distally to the larger cylindrical introducer portion 318. The introducer 318 has a large opening through which the catheter 310 slides into a urethra. A sachet 340 is contained within the sheath 312 and external to the catheter 310. In this exemplary embodiment, the sheath 312 is directly adhered to the distal portion 319 of the introducer 318, through a collar, heat shrink or other mechanism, as shown in FIG. 3, and appreciated by one having ordinary skill in the art. The use, function, and mechanism of operation of this embodiment is substantially the same as that described above for the embodiment shown in FIGS. 1-2, so it will not be repeated here again for sake of clarity.

In some exemplary embodiments of the present subject disclosure, the introducer 114 is shaped such that it may be more easily gripped in one hand while the catheter cap 100 is being removed with the opposite hand. For example, the introducer may be larger in size, such that one with limited manual dexterity can grip the introducer. Further, the angle of the introducer may be such that it may be used to pull in one direction as the cap 100 is pulled in the opposite direction.

In exemplary embodiments of the present subject disclosure, the catheter cap 100 is filled with the lubricant or gel before being coupled to the introducer tip. This may help to ensure that the external surface of the introducer tip is properly lubricated. The internal surface of the introducer tip may be further lubricated when the catheter cap is pulled off, as the stopper may draw lubrication from the introducer and into the introducer tip during cap removal. Thus, when the catheter is being inserted through the introducer tip, the introducer tip contributes to the lubrication of the catheter instead of scraping off the lubrication.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A catheter system for draining a fluid, the system comprising:
   a catheter having an uncoated surface;
   an introducer coupled to a proximal end of the catheter, the introducer having a tip which is covered by a lubricant with a viscosity of greater than 2,000 cP;
   a sheath surrounding the catheter; and
   a pliable plastic foil sachet positioned loosely within the sheath and external to the catheter, the sachet containing a water-based gel having a viscosity of less than 2,000 cP.

2. The system in claim 1, wherein the sachet decreases evaporation and is capable of being opened by tearing or bursting open with normal manual forces applied outside of the sheath without compromising the sheath.

3. The system in claim 2, wherein the pliable plastic does not interfere with scrunching of the sheath during catheter deployment.

4. The system in claim 1, further comprising a collection bag positioned at one end of the catheter.

5. The system in claim 4, further comprising finger holes positioned in the collection bag to facilitate in opening of the collection bag.

6. The system in claim 4, further comprising a hook positioned near the connection of the catheter to the collection bag.

7. The system in claim 1, further comprising an elongate stem insertable into the introducer.

8. The system in claim 7, further comprising a stopper coupled to a distal end of the elongate stem, the stopper sealing a distal portion of the introducer.

9. The system in claim 8, further comprising a cap coupled to a proximal end of the elongate stem such that the cap covers the introducer tip protruding from a proximal end of the introducer; and wherein the lubricant is contained within the cap and covers the introducer tip when within the bell cap.

10. The system in claim 9, wherein the cap and stopper seal the introducer when coupled with the introducer.

11. The system in claim 8, wherein the stopper is substantially spherical.

12. The system in claim 8, wherein the stopper is a radial flange.

13. The system in claim 12, wherein the radial flange has a beveled edge.

14. The system in claim 8, wherein the distal opening releasably engages with the stopper.

15. A catheter system for draining a fluid, the system comprising:
   a catheter having an uncoated surface;
   an introducer coupled to a proximal end of the catheter, the introducer having a tip which is covered by a lubricant with a viscosity of greater than 2,000 cP;
   a sheath surrounding the catheter;
   a collection bag positioned at one of the catheter; and
   a pliable plastic foil sachet comprised of a pliable plastic foil type and positioned loosely within the sheath and external to the catheter, the sachet containing a water-based gel having a viscosity of less than 2,000 cP.

16. A catheter system for draining a fluid, the system comprising:
   a catheter having an uncoated surface;
   a sheath surrounding the catheter;
   a collection bag positioned at one of the catheter;
   an introducer coupled to a proximal end of the catheter, the introducer having a tip which is covered by a lubricant with a viscosity of greater than 2,000 cP, the introducer in liquid communication with a volume between the sheath and the catheter; and
   a pliable plastic foil sachet comprised of a pliable plastic foil type and positioned loosely within the sheath and external to the catheter, the sachet containing a water-based gel having a viscosity of less than 2,000 cP.

17. The system in claim 1, wherein the lubricant has a viscosity of 15,000-30,000 cP.

18. The system in claim 1, wherein the lubricant has a viscosity of 18,000-26,500 cP.

19. The system in claim 15, wherein the lubricant has a viscosity of 15,000-30,000 cP.

20. The system in claim 16, wherein the lubricant has a viscosity of 15,000-30,000 cP.

* * * * *